(12) United States Patent
Madrid et al.

(10) Patent No.: US 8,497,361 B2
(45) Date of Patent: Jul. 30, 2013

(54) TOPOISOMERASE BINDING PROBE AND METHOD OF USE

(75) Inventors: Peter Madrid, San Francisco, CA (US); Bryan Glaser, San Francisco, CA (US); Jeremiah Malerich, San Francisco, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 13/215,175

(22) Filed: Aug. 22, 2011

(65) Prior Publication Data

US 2012/0225788 A1    Sep. 6, 2012

Related U.S. Application Data

(60) Provisional application No. 61/376,111, filed on Aug. 23, 2010.

(51) Int. Cl.
*C07H 15/203* (2006.01)
*C07D 311/50* (2006.01)
*C07D 405/12* (2006.01)

(52) U.S. Cl.
CPC ............ *C07H 15/203* (2013.01); *C07D 405/12* (2013.01); *C07D 311/50* (2013.01)
USPC ............................. 536/13; 536/17.9; 549/285

(58) Field of Classification Search
None
See application file for complete search history.

(56) References Cited

U.S. PATENT DOCUMENTS 6,916,846 B2 *   7/2005   Farrar et al. .................... 514/457

OTHER PUBLICATIONS

Shen et al., "Syntheses of photolabile novobiocin analogues" Bioorganic and Medicinal Chemistry Letters (2004) vol. 14 pp. 5903-5906.*
Budin et al., "A Chemical Labeling Strategy for Proteomics under Nondenaturing Conditions" Communications (2010) vol. 11 pp. 79-82.*

* cited by examiner

*Primary Examiner* — Eric S Olson
(74) *Attorney, Agent, or Firm* — Richard Aron Osman

(57) ABSTRACT

An aminocoumarin conjugated to a fluorescent label through a secondary amine, is operative as a fluorescent polarization probe of the DNA gyrase B or topoisomerase IV E subunit. The probe is used for detecting topoisomerase inhibitor binding by fluorescence polarization, particularly in a high-through put topoisomerase inhibitor assay.

20 Claims, 9 Drawing Sheets

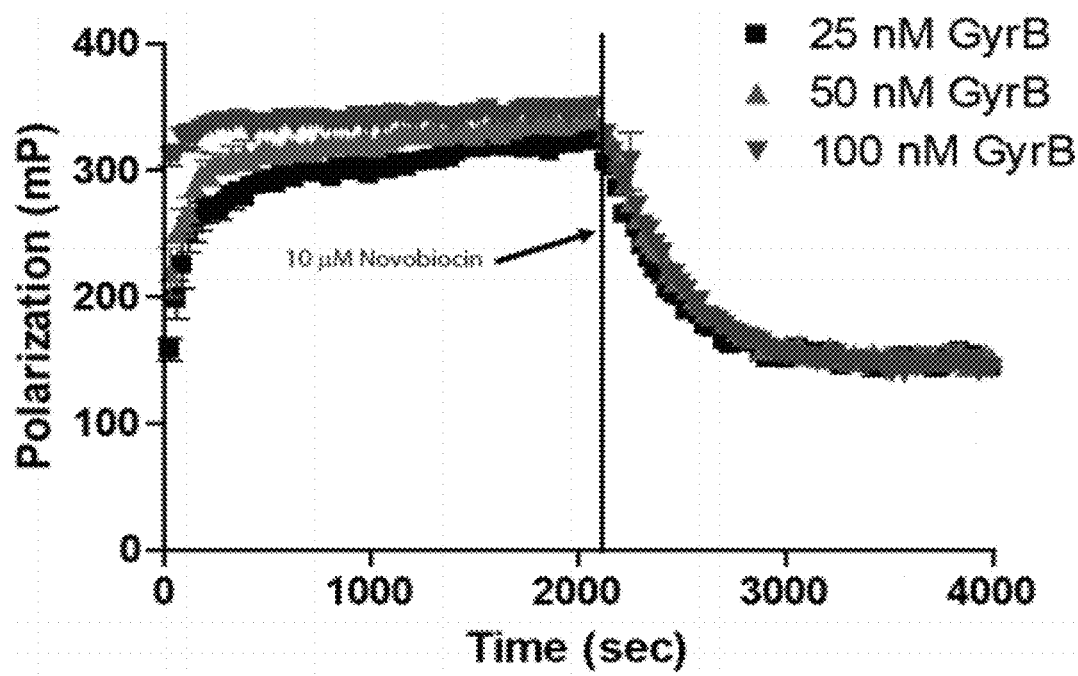

TOPOISOMERASE BINDING PROBE AND METHOD OF USE

Figure 1A:
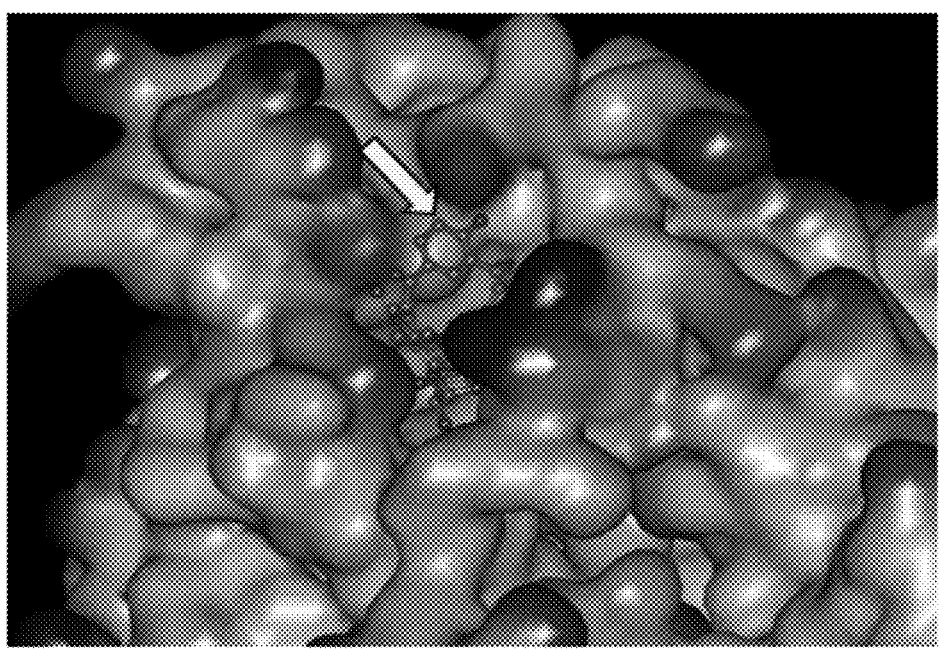

This application claims priority to U.S. Ser. No. 61/376,111, filed Aug. 23, 2010 by the same inventors.

This work was supported by grants No. 1 U01 AI082070-01 from the NIH NIAID; the Government has certain rights in this invention.

FIELD OF THE INVENTION

The field of the invention is a fluorescent topoisomerase binding probe and method of use.

BACKGROUND OF THE INVENTION

DNA gyrase is an essential type II topoisomerase that catalyzes the introduction of negative supercoils using the free energy of ATP hydrolysis. The enzyme is composed of two subunits, Gyrase A (GyrA) and Gyrase B (GyrB), that form a functional heterotetramer $A_2B_2$ required for bacterial viability. The GyrA subunit is targeted by synthetically developed quinolone antibiotics, which have broad-spectrum activity against both gram-positive and gram-negative bacteria. The GyrB subunit is targeted primarily by natural product antibiotics such as the aminocoumarin antibiotics, e.g., novobiocin and coumermycin[1], as well as cyclothialidine[2]. Mutations that confer drug resistance to all three antibiotics have been reported[3,4]. Mutations associated with both coumarin and cyclo-thialidine resistance map to the periphery of the ATP binding site of GyrB that hydrolyzes ATP[5]. The emergence of bacterial strains resistant to existing antibiotics makes it imperative to develop new classes of antibiotics that take into account these known mutations and, to the extent possible, restrict their mode of action to portions of the enzyme that are conserved by functional necessity. Residues required for coupling ATP hydrolysis to DNA supercoiling in GyrB have been identified using site-directed mutagenesis[5]. Along with this extensive mutational data, analysis of high-quality crystal structures suggests the value of pursuing next-generation GyrB inhibitors that target the ATP-binding domain[6]. The ATP binding site within GyrB is highly conserved across bacterial species and is not present in humans, making it suitable for the development of broad-spectrum antibiotics.

Because the bacterial gyrase holoenzyme has been the subject of multiple drug discovery efforts, many assays exist to measure its activity. Assays used for general studies of the holoenzyme as well as many high-throughput screens measure the ability of the enzyme to convert relaxed DNA into supercoiled DNA. Most of these studies use an assay that couples ATP hydrolysis to NADH, resulting in a measureable colorimetric change[2,5,6]. Similar assays directly measure the total level of supercoiled DNA using agarose-gel separations or fluorescence dyes[7-9]. Cell-based assays that measure the level of DNA damage have also been used to measure gyrase activity[10]. Although all of these assays can be used to measure the activity of the gyrase holoenzyme, they often require multiple addition steps, cannot separate GyrA from GyrB inhibitors, and do not focus on the ATP-binding domain. One assay has been described that measures the direct binding of [$^3$H]dihydronovobiocin to a biotin-labeled 43-kDa fragment of GyrB using a scintillation proximity assay (SPA)[10]. While the SPA directly examines the ATP-binding domain, an assay that does not require radioactivity would be more suitable for high-throughput screening (HTS).

Fluorescence polarization (FP) is a homogeneous assay that can be used to measure the binding interaction between two molecules[11]. FP is based on the principle that a fluorophore excited by polarized light will also emit polarized light. Molecular motion, which is dependent on the size of the molecule, causes depolarization of the light by radiating at a different direction than the incident light. A small unbound fluorescent probe rotates rapidly and maintains low levels of polarization after excitation. If the fluorescent probe binds to a larger molecule, such as a protein, forming a stable complex, the bound probe rotates more slowly and increases the amount of polarized light. Binding is directly related to the polarization level of the sample: an unbound fluorescent probe has low FP and a bound fluorescent probe has high FP. The FP assay is well suited for measuring the interaction of two molecules in real time and is commonly used in HTS[12].

This patent presents the development and optimization of a novel FP assay to detect competitive inhibitors of the ATP-binding domain of GyrB and structurally-related topoisomerases. We have designed and synthesized a novel fluorescent probes by covalently attaching a fluorophores to novobiocin guided by the GyrB/novobiocin crystal structure (Protein Data Bank entry 1KIJ)[13]. Experiments were performed to develop the FP assay and optimize the use of the conjugates to measure the competition for binding to the ATP-binding domain of GyrB. We have determined the kinetics and strength of the interaction of the conjugates with GyrB as well as the effect of common buffer additives on the interaction. The assay was also validated for use in HTS for inhibitors of the ATP-binding domain by screening a small library of FDA-approved compounds. This screen identified a known GyrB inhibitor as well as four members of the anthracycline family of cancer therapeutics (doxorubicin, idarubicin, epirubicin, and daunorubicin).

The subject probe conjugates were nonobvious and their use in FP assays was unexpected. Labeling small-molecule ligands with fluorescent dyes is uncommon for FP assays, since the labeling chemistry often results in substantial increases in molecular weight and alterations of molecular properties. Our design strategy was to utilize a natural product aminocoumarin that tightly binds into the ATP binding site of the topoisomerase, and tether a fluorescent dye off of a solvent-exposed position of the molecule. We studied the crystal structure of novobiocin bound to GyrB and determined that most of the ligand is deeply buried within the protein active site, with the exception of the phenolic benzamide ring, so our proposed modification was modeled in the active site to confirm solvent accessibility of the attached moiety. Since the phenol group was directly interacting with an aspartic acid residue, we hypothesized that the ortho position of this ring would be a good position at which to attach a fluorescent labeling group. We specifically labeled this position of novobiocin using a Mannich reaction, which is selective for aromatic ring positions ortho to a phenol group, and under neutral conditions, as we knew that novobiocin degrades under either basic or acidic conditions.

Topoisomerase IV is a bacterial type II topoisomerase of similar structure and function: it also utilizes the free energy from ATP hydrolysis to catalyze topological changes in the bacterial genome, has the same subunit structure—wherein the subunits corresponding to the gyrase subunits A and B are named C and E (Bellon et al. Antimicrob Agents Chemother 2004, May, 48(5), 1856-64) and is similarly inhibited by aminocoumarins and targeted by the subject probes.

Aspects of this disclosure were published by us in: Glaser et al., J Biomol Screen. 2011 February; 16(2):230-8. Epub 2011 Jan. 18, entitled "A high-throughput fluorescence polarization assay for inhibitors of gyrase B."

SUMMARY OF THE INVENTION

The invention provides methods and compositions for detecting and assaying topoisomerase inhibitor binding. In one aspect the invention provides a fluorescence polarization probe comprising an aminocoumarin conjugated to a fluorescent label, said probe operative as a fluorescent polarization probe of the ATP-binding site of prokaryotic DNA gyrase B or topoisomerase IV E subunit.

In particular embodiments, the amino coumarin is characterized as a 3-amino-4,7-dihydroxycumarin ring, which is linked with a sugar in 7-position and a benzoic acid derivative in 3-position, and the fluorescent label is conjugated at the benzoic acid moiety, particularly through an amide bond.

In particular embodiments, the aminocoumarin is novobiocin or chlorobiocin, the fluorescent label is an acridine, a cyanine, a fluorone, an oxazin, a phenanthridine, a rhodamine or a BODIPY (boron-dipyrromethene), and/or the subunit is of *Staphylococcus aureus, Escherichia coli*, or *Francisella tularensis*, particularly the gyrase, B subunit of *Francisella tularensis*.

In another aspect the invention provides a method of making a subject probe, comprising the step(s) of conjugating the label through a reactive secondary amine of an aminocoumarin amine to form the probe, and optionally, the antecedent step of attaching the reactive secondary amine to the aminocoumarin through a Mannich reaction to form the aminocoumarin amine.

In another aspect, the invention provides a method of detecting binding of a subject probe to the subunit, which may be part of a dimeric or heterodimeric complex, comprising the step of: detecting fluorescence polarization of the probe in a mixture of the probe and the subunit. In particular embodiments, the subunit is the gyrase, B subunit of *Francisella tularensis*, and/or the mixture further comprises a topoisomerase inhibitor that inhibits binding of the probe to the subunit, optionally wherein the method is in a high-throughput format and repeated in parallel with a plurality of candidate topoisomerase inhibitors.

The invention provides all combinations of specifically recited particular embodiments or elements as if each combination had been specifically recited.

BRIEF DESCRIPTION OF THE FIGURES

FIG. 1A: The crystal structure of novobiocin bound to the ATP-binding domain of *Thermus thermophilus* Gyrase B.

FIG. 1B: The synthesis of Novo-TRX.

FIG. 2: Equilibration studies of the interaction of Novo-TRX and GyrB.

FIG. 3: $K_D$ measurements for the interaction of Novo-TRX with GyrB.

FIG. 4: The effect of common additives on the binding of Novo-TRX to GyrB.

FIG. 5: HTS of FDA-approved drugs for inhibitors of Novo-TRX binding to GyrB.

FIG. 6: The $K_1$ of hits from the HTS.

FIG. 7: A secondary Gyr activity assay to confirm hits from the HTS.

DETAILED DESCRIPTION OF SPECIFIC EMBODIMENTS OF THE INVENTION

In one aspect the invention provides a fluorescence polarization probe comprising an aminocoumarin conjugated to a fluorescent label, said probe operative as a fluorescent polarization probe of the ATP-binding site of prokaryotic DNA gyrase B or topoisomerase IV E subunit.

Aminocoumarins are art-recognized antibiotics that work by competitive inhibition of energy transduction of DNA gyrase by binding to the ATPase active site located on the GyrB or topo IV E subunit—well-known examples include novobiocin and chlorobiocin. Suitable operative aminocoumarins may also be selected from the numerous analogs known in the art, e.g.:

Heide L., Biotechnol Adv. 2009 November-December; 27(6): 1006-14. Epub 2009 May 20, Genetic engineering of antibiotic biosynthesis for the generation of new aminocoumarins;

Heide L., Methods Enzymol. 2009; 459:437-55. Aminocoumarins mutasynthesis, chemoenzymatic synthesis, and metabolic engineering;

Alt S, Mitchenall L A, Maxwell A, Heide L., J Antimicrob Chemother. 2011 September; 66(9):2061-9. Epub 2011 Jun. 21. Inhibition of DNA gyrase and DNA topoisomerase IV of *Staphylococcus aureus* and *Escherichia coli* by aminocoumarin antibiotics; and Anderle C, Stieger M, Burrell M, Reinelt S, Maxwell A, Page M, Heide L. Antimicrob Agents Chemother. 2008 June; 52(6):1982-90. Epub 2008 Mar. 17, Biological activities of novel gyrase inhibitors of the aminocoumarin class;

see also: US 20090187014 and US 20090163709.

In particular embodiments the aminocoumarin comprises a substituted phenol moiety that is joined though the secondary amine to the fluorescent label. In other embodiments the aminocoumarin is of the general Formula I, as disclosed by Anderle et al. (supra):

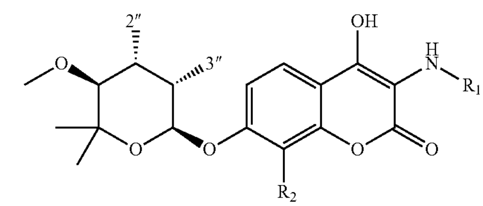

wherein $R_1$ is selected from the group consisting of:

;

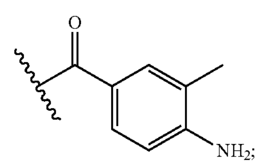

;

;

;

;

;

;

;

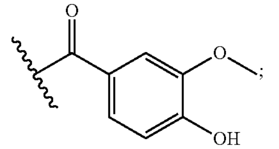

;

-continued

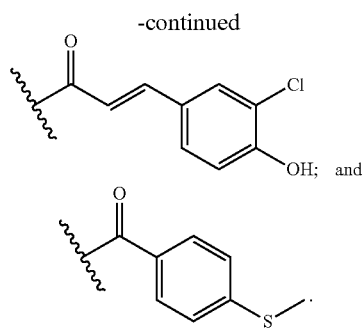

$R_2$ is H, Cl, or Me; 2" is pyrrole or OH; and 3' is pyrrole or OH.

We have also exemplified operative probes with a diverse variety of fluorescent labels, showing that the aminocoumarin moiety and coupling chemistry are tolerant to alternative labels. Hence, the subject probes can be equivalently constructed and used with alternative labels suitable to fluorescent polarization assays, including acridines, cyanines, fluorones (including fluorescein and fluorscein derivatives and analogs), oxazins, phenanthridines, rhodamines (including ALEXA dyes), and BODIPY (boron-dipyrromethenes), etc. Preferred dyes have molecular weights less than 3,000 Da, 2,000 Da, or 1,500 Da.

Exemplary validated probe syntheses with three different dyes is shown here:

A. Synthesis of Nova-BODIPY

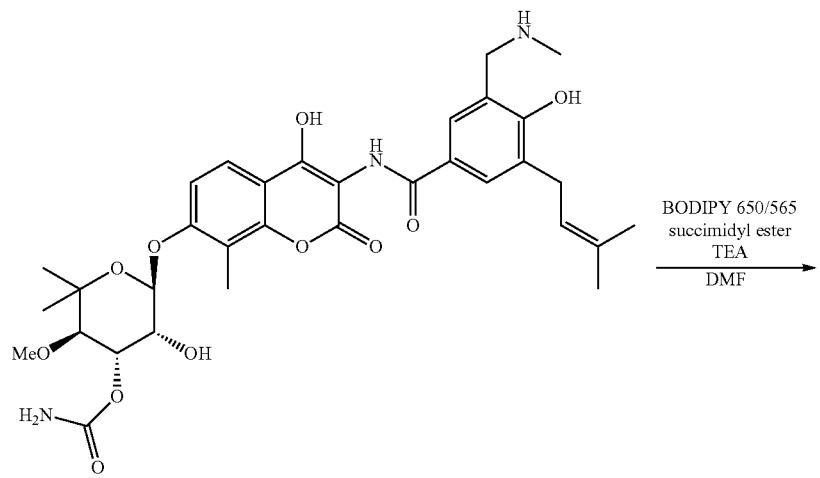

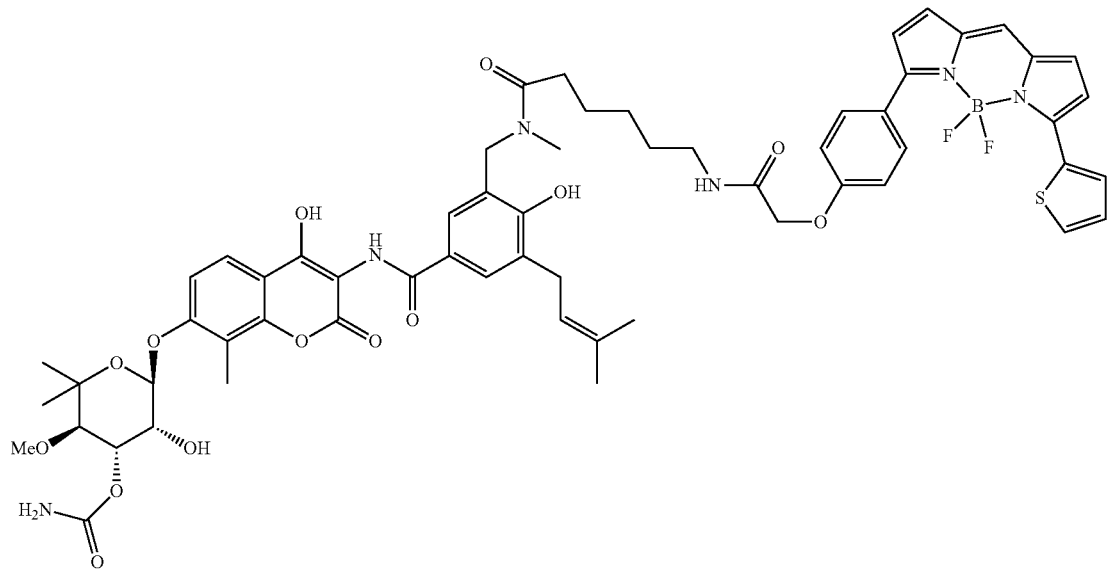

Novo-BODIPY

B. Synthesis of Novo-Cy3
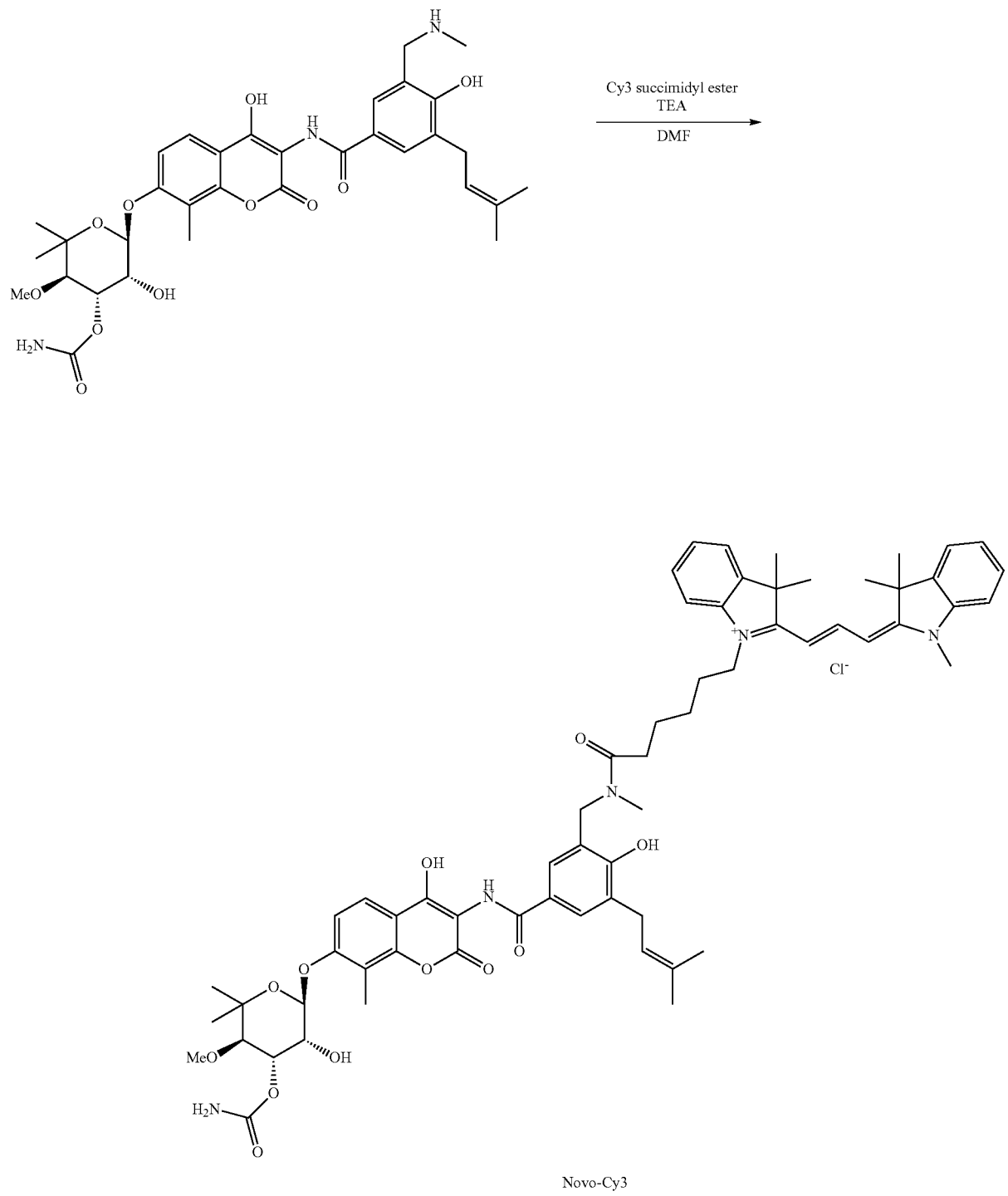
Novo-Cy3

C. Synthesis of Novo-ALEXA

[Chemical structure of aminocoumarin-amine intermediate]

ALEXA 594
succinimidyl ester
TEA
―――――――→
DMF

[Chemical structure of Novo-ALEXA product]

Novo-ALEXA
(5,6 isomers)

In another aspect the invention provides a method of making a subject probe, comprising the step(s) of conjugating the label through a reactive secondary amine of an aminocoumarin amine to form the probe, and optionally, the antecedent step of attaching the reactive secondary amine to the aminocoumarin through a Mannich reaction to form the aminocoumarin amine. The chemistry should avoid acidic and basic conditions or high temperatures that would otherwise degrade the aminocoumarin.

In another aspect, the invention provides a method of detecting binding of a subject probe to the subunit, comprising the step of: detecting fluorescence polarization of the probe in a mixture of the probe and the subunit. Aminocoumarins have been found to bind the ATP binding site of GyrB/TopoIVE submits across species; hence, the subject probes can be equivalently used to assay amniocoumarin-binding GyrB/TopoIVE subunits derived from alternative species, such as *Staphylococcus aureus*, *Escherichia coli*, and *Francisella tularensis*.

In particular embodiments, the mixture further comprises a topoisomerase inhibitor that inhibits binding of the probe to the subunit, optionally wherein the method is in a high-throughput format and repeated in parallel with a plurality of candidate topoisomerase inhibitors; hence, the probe may be used to screen chemical libraries for inhibitors of topoisomerase.

EXAMPLES

High-Throughput Fluorescence Polarization Assays for Inhibitors of Gyrase B.

Here we demonstrate our development of a novel FP assay that specifically measures competition for binding to the ATP-binding domain of GyrB. The assay uses a novel binding probe, Novo-TRX, which is composed of a long-wavelength fluorescent dye conjugated to the known ligand novobiocin. This homogenous, non-radioactive assay has been optimized for screening in a 384-well format and has demonstrated robust assay statistics (Z'=0.80). The stability of Novo-TRX has been demonstrated to be suitable for real-time binding kinetics studies and can be used to determine the binding kinetics of potential inhibitors. The high level of conservation in the ATP-binding domain suggests that the Novo-TRX probe would be a valuable tool to study the GyrB of any bacterial species. This new methodology has been successfully used to rapidly screen a small library of compounds, and a novel mechanism for the direct inhibition of bacterial gyrase by the anthracyclines was identified and confirmed using a secondary activity assay.

Design of FP Assay for GyrB

Although enzymatic assays for GyrB exist, an equilibrium binding assay suitable for HTS would have several advantages. Since the holoenzyme is a heterotetramer ($A_2B_2$), enzymatic assays require the recombinant production of both the GyrA and GyrB subunits and then subsequent mixing to form the complex. The enzymatic assays have the potential to identify inhibitors at multiple binding sites. A homogeneous equilibrium binding assay, such as FP, requires minimal reagent addition steps and can be used to efficiently identify inhibitors of the GyrB ATP-binding site in an HTS format.

The assay design strategy was to utilize the natural product novobiocin, which is known to tightly bind into the ATP binding site of GyrB, and tether a fluorescent dye off of a solvent-exposed position of the molecule. Labeling small-molecule ligands with fluorescent dyes is less common for FP assays, since the labeling chemistry often results in substantial increases in molecular weight and alterations of molecular properties. In the case of novobiocin, we hypothesized that such an approach would be feasible since the ligand is relatively large (612 Da) and crystal structures of novobiocin bound to GyrB have revealed the precise binding mode of the ligand, which can be used to identify optimal attachment points. A key advantage of such a system is that the size discrepancy between novobiocin (<1 kDa) and the full-length GyrB (92.5 kDa) should be reflected by a large change in polarization values upon binding.

Design and Synthesis of Novo-TRX

The crystal structure of novobiocin bound to GyrB (PDB entry 1KIJ) reveals that most of the molecule is deeply buried within the protein active site, with the exception of the phenolic benzamide ring, and the proposed modification was modeled in the active site to confirm solvent accessibility of the attached moiety (FIG. 1A). Since the phenol group was directly interacting with an aspartic acid residue (Asp80 on 1KIJ), the ortho position of this ring was the ideal position at which to attach a fluorescent labeling group. This position of novobiocin was specifically labeled using a Mannich reaction, which is selective for aromatic ring positions ortho to a phenol group, and can be carried out under neutral conditions. Novobiocin is known to degrade under either basic or acidic conditions, so the neutral conditions of the Mannich reaction were ideal for the conjugation chemistry.

Figure 1B:
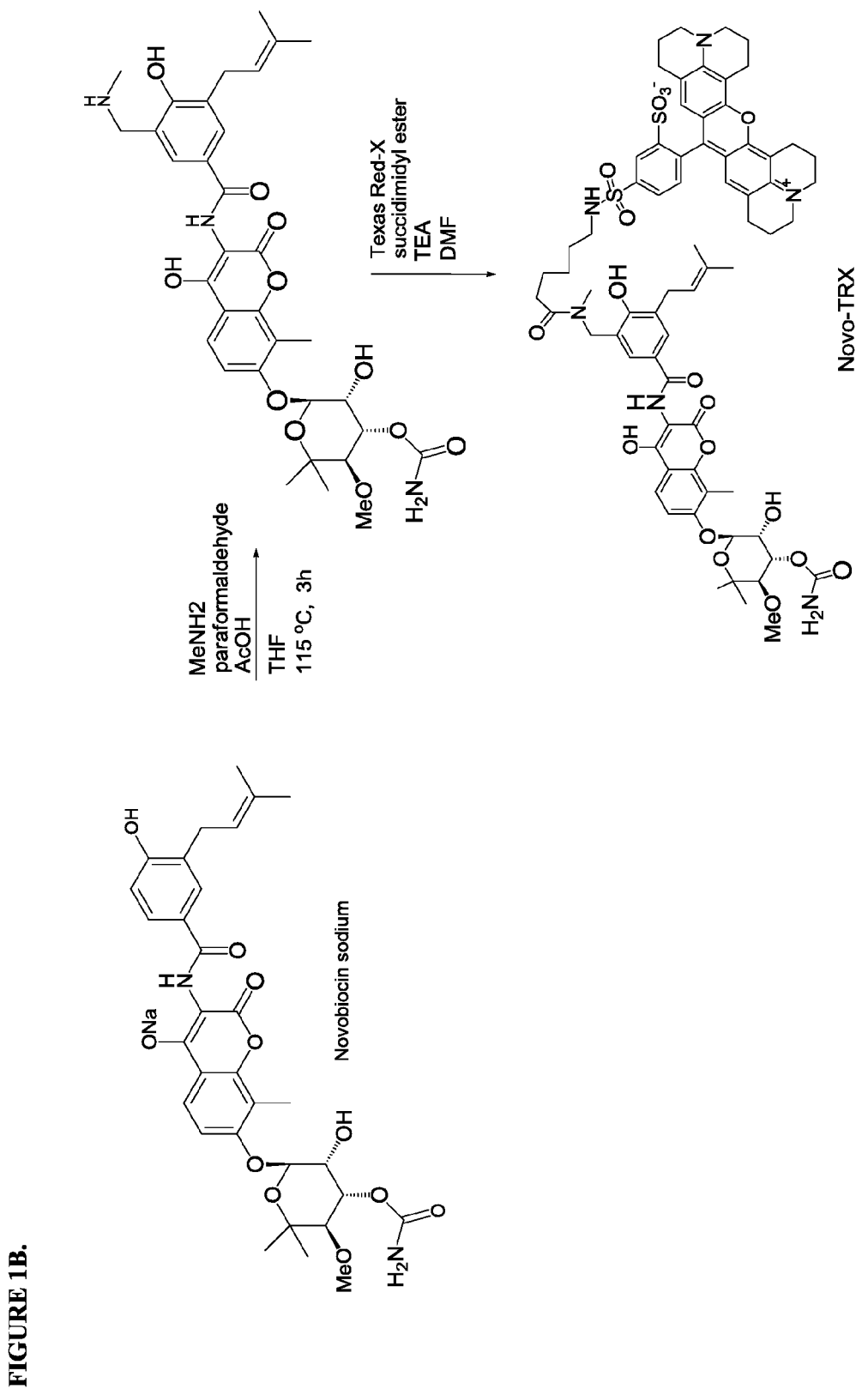

The novobiocin sodium reacted with formaldehyde and methyl-amine to give a reactive novobiocin methylamine intermediate that could be conjugated to various electrophilic fluorescent dyes (FIG. 1B). The novobiocin derivative was coupled to the long-wavelength rhodamine derivative, Texas Red, since its excitation/emission maxima (595/615 nm) are in a range that reduces the chances of optical interference from screening compounds. The novobiocin methylamine was reacted with Texas Red-X succinimidyl ester with base and then purified using HPLC to yield the pure probe Novo-TRX.

Equilibrium Binding Experiment

Kinetic experiments were performed to determine the time needed for the binding of Novo-TRX to GyrB to reach equilibrium. The experiment examined both the association and dissociation components of the interaction in real time (FIG. 2). To begin, increasing concentrations of GyrB (25, 50, and 100 nM) were mixed with 40 nM Novo-TRX and the FP signal was monitored every 30 seconds until equilibrium was reached. The binding of Novo-TRX to GyrB results in an increase in the FP signal over time. As anticipated, the rate of association was faster with higher concentrations of GyrB. For all reactions, equilibrium was reached by 1000 seconds (~17 minutes). To establish that the observed binding was specific, a 125-fold excess (10 µM) of unlabeled novobiocin was added to the samples and the change in FP signal was measured in real time. The large excess of unlabeled novobiocin was able to compete better than the Novo-TRX for binding to GyrB, and the FP signal decreased overtime. As with the association experiments, the new binding equilibrium was reached by roughly 1000 seconds after the addition of the unlabeled novobiocin. A one-phase exponential decay equation was used to determine that the average half-life of dissociation was 230 seconds for the three concentrations of GyrB; the association reaction was too fast to determine accurate rates. The ability to monitor binding events in real time in a homogenous solution is a major advantage of FP over other binding assays that require a separation step to measure the interaction. Binding experiments, including the HTS, were incubated for 60 minutes before the FP signal was measured, to guarantee that equilibrium had been reached in the assay.

Saturation Binding Experiment

Figure 3:
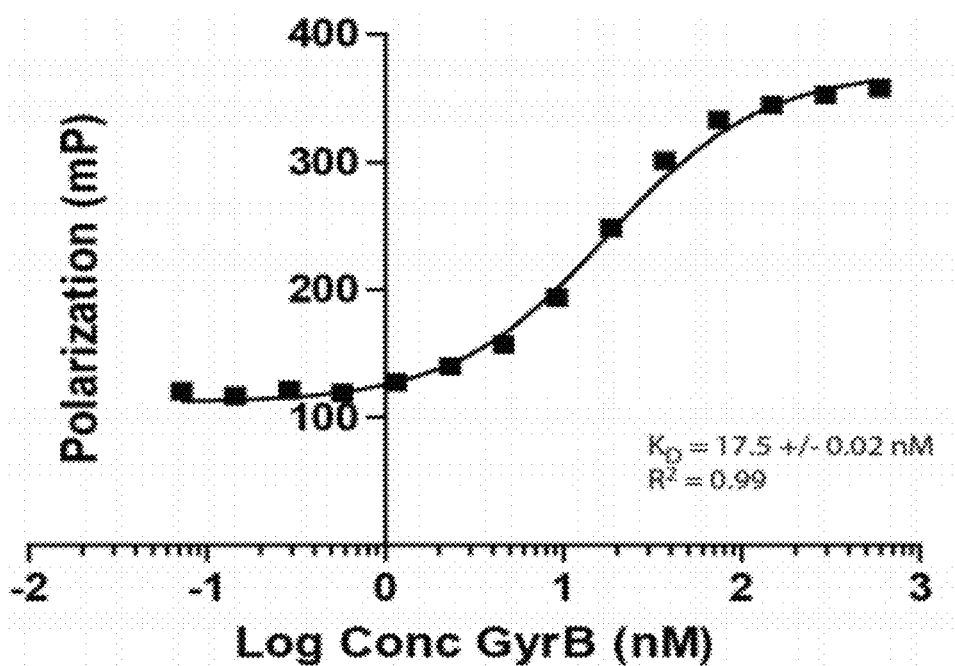

Saturation binding experiments were performed to determine the strength of the interaction of Novo-TRX with GyrB and to analyze if the addition of the Texas Red-X fluorophore to novobiocin resulted in a gain or loss of binding strength. To determine the strength of the interaction of Novo-TRX with GyrB, increasing concentrations of GyrB were incubated with 40 nM Novo-TRX for 1 hour to ensure that the binding was at equilibrium. Based on the crystal structure, we predicted that the addition of the fluorophore would result in a minimal perturbation of the binding. The resulting binding data were fit, and the $K_D$ was calculated to be 17.5±0.02 nM (FIG. 3). The binding of Novo-TRX was similar to published results for the interaction of novobiocin with a 43 kDa fragment of E. coli gyrase[16]. Beyond verifying the interaction of Novo-TRX with GyrB, the saturation curve was also used to determine the concentrations of GyrB and Novo-TRX that would be most suitable for the assay in a HTS. Concentrations that resulted in ~80% saturation of binding were chosen.

Solvent Susceptibility Experiment

Figure 4A:
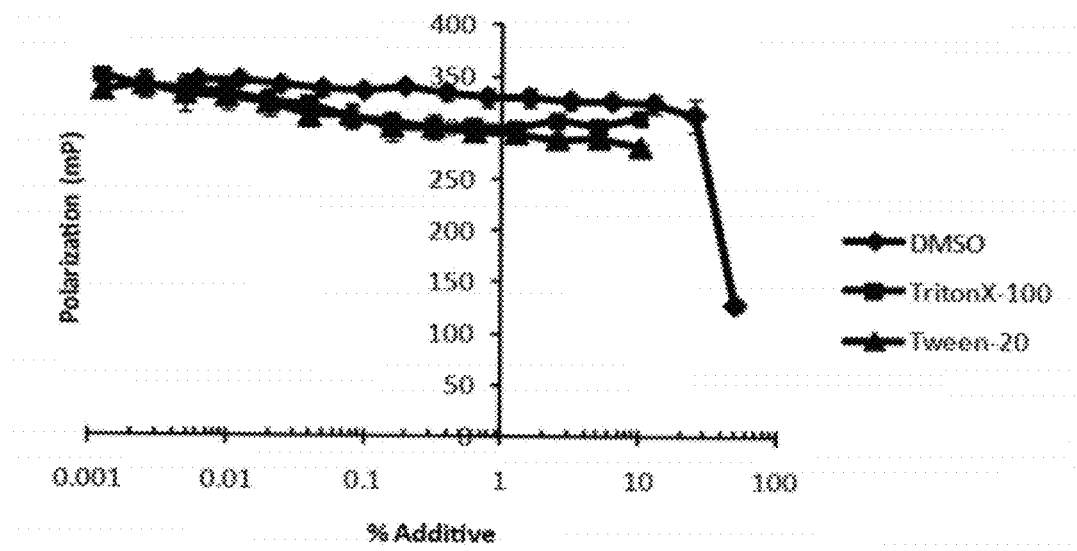
Figure 4B:
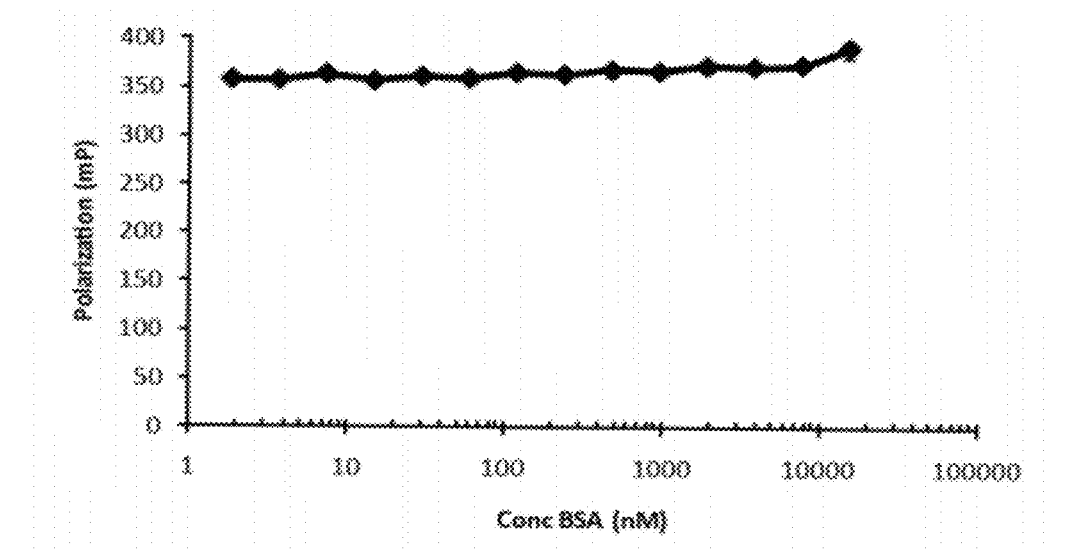

Before performing HTS, we tested common solvents and additives for their effect on the binding of Novo-TRX to GyrB using the FP binding assay. The concentration of 40 nM Novo-TRX and 40 nM GyrB were chosen so that binding was roughly 80% saturated. The complex was then incubated with increasing concentrations of DMSO, TritonX-100, Tween-20, and BSA. DMSO, which is commonly used as a solvent for the compounds in a chemical library, had a minimal effect on binding at percentages up to 10% (v/v). Understanding what levels of DMSO could be tolerated by the assay was important, especially in an HTS for small fragments that may have low affinity for the binding site and will need to be tested at higher concentrations (>50 µM). The non-ionic detergents, TritonX-100 and Tween-20, also only slightly perturbed binding even at percentages close to 10% (FIG. 4A). Additional studies using the detergents in saturation binding experiments demonstrated that the detergents significantly raised the background of the assay. It is likely that the level of the signal observed at the highest concentrations of the detergents is equivalent to the background caused by the detergent. It is also possible that the detergents were able to bind to Novo-TRX and increase the FP signal. BSA was well tolerated in the assay up to concentrations around 1 µM; higher concentrations resulted in non-specific binding (FIG. 4B).

High-Throughput Screening of a Small Chemical Library

As a proof-of-principle test for the ability of the FP assay to identify inhibitors of the *F. tularensis* GyrB at the ATP-binding domain, the assay was used to screen a small chemical library consisting of 1040 FDA-approved compounds and 80 additional antibiotics (FIG. 5A-D). The library was large enough to test the statistical robustness of the assay using multiple liquid handlers that would be required for a large-scale screen. The library was chosen because novobiocin was present in multiple locations and would serve as a positive control in the HTS. The compounds were screened at a concentration of 10 μM against a complex of 40 nM Novo-TRX and 40 nM GyrB in 5% DMSO. The Z'-factor, Z-factor, and signal-to-noise (S/N) and signal-to-background (S/B) ratios were calculated as described by Zhang et al[15]. The window of the assay (the distance between the high and low controls), along with the highly consistent data points, resulted in a very robust, reproducible screen (Z'=0.8). Eight compounds were identified that decreased the binding of 40 nM Novo-TRX to 40 nM GyrB by greater than 40%: the four internal novobiocin controls and four members of the anthracycline family of cancer chemotherapeutics (doxorubicin, idarubicin, epirubicin, and daunorubicin). This family is known to have anti-topoisomerase II activity, although it is thought that this activity is through DNA intercalation[17-20].

Dose-Response Experiment

The ability of the hits from the HTS to prevent the interaction of Novo-TRX with GyrB was confirmed using a dose-response experiment. Increasing concentrations of the compounds were incubated at room temperature for 1 hour with 40 nM Novo-TRX and 40 nM GyrB before the FP signal was measured. The $K_1$ was determined by fitting the data using the sigmoidal dose-response equation to determine the $IC_{50}$, as described above (FIG. 6). The $K_1$ was then calculated by GraphPad Prism 4 using the $IC_{50}$, concentration of Novo-TRX, and the $K_D$ of the interaction of Novo-TRX with GyrB (17.5 nM). The $K_1$ was determined to be 11, 94, 386, 480, and 444 nM for novobiocin, doxorubicin, epirubicin, idarubicin, and daunorubicin, respectively.

Gyrase Activity Assay

The hits were tested in a secondary activity assay to determine if they could prevent the conversion of relaxed plasmid DNA to supercoiled DNA by an *E. coli* gyrase $A_2B_2$ heterotetramer. Initial experiments tested the activity of 10 μM of each compound in preventing the supercoiling of 1.0 μg of relaxed DNA. As anticipated, novobiocin was able to completely prevent supercoiling by the gyrase holoenzyme while none of the anthracycline compounds were able to prevent supercoiling. The lack of activity of the anthracyclines was particularly surprising because the compounds are documented to intercalate into DNA and have anti-topoisomerase II activity[18-20]. The ability of the compounds to directly cause DNA supercoiling along with both the gyrase and DNA competing for binding to the anthracyclines, which would result in lower concentrations of compound, most likely resulted in the false-negative activity in the first conditions tested[21; 22]. In a second set of experiments, the holoenzyme was incubated with 50 μM of each compound and 0.5 μg of the relaxed DNA for 1 hour at 37° C. and the amount of supercoiling was analyzed by agarose-gel electrophoresis and ethidium bromide staining (FIG. 7). DMSO was used as a vehicle control, and pre-supercoiled DNA alone was loaded as a negative control. A second set of reactions without the gyrase holoenzyme was used to control for supercoiling caused by the compound treatment. Under the second set of conditions, doxorubicin and epirubicin were able to inhibit supercoiling to the level of the no gyrase control. The activity of idarubicin and daunorubicin is less clear because the level of supercoiling caused by the treatment alone is comparable to the level of supercoiling with the gyrase. While the members of the anthracycline family are known eukaryotic topoisomerase II poisons, they have not previously been reported to directly inhibit the ATP binding domain.

In subsequent experiments we developed analogous probes with alternative fluorescent labels, including BIODIPY, cyanine (Cy3) and ALEXA dyes, and confirmed their utility in high throughput FP assays.

DETAILED DESCRIPTION OF THE FIGURES

FIG. 1: The design and synthesis of Novo-TRX as a fluorescence polarization probe for GyrB. A) The crystal structure of novobiocin bound to the ATP-binding domain of *Therms thermophilus* Gyrase B (PDB entry 1KIJ). The arrow indicates the site of attachment of the Texas Red-X succidimidyl ester to novobiocin. B) The synthesis of Novo-TRX.

FIG. 2: Equilibration studies of the interaction of Novo-TRX and GyrB. Kinetic experiments were performed to determine the time needed for binding of Novo-TRX and GyrB to reach equilibrium. Equal volumes of 2X Novo-TRX were mixed with 2X GyrB to result in a final concentration of 40 nM Novo-TRX and 25, 50, or 100 nM GyrB and the polarization was measured every 30 seconds for 70 cycles. The FP signal (mP) and the error bars represent the data from four replicates. To measure the dissociation of Novo-TRX, 125-fold unlabeled Novobiocin was added to the Novo-TRX/GyrB samples resulting in a final concentration of 10 μM. The change in FP was measured every 30 seconds for 70 cycles. The average FP signal (mP) for four replicates was determined and the error bars represent the standard deviation.

FIG. 3: $K_D$ measurements for the interaction of Novo-TRX with GyrB. The homogeneous binding of Novo-TRX to GyrB was measured under equilibrium conditions to determine the strength of the interaction ($K_D$). Increasing concentrations (0-2500 nM) of GyrB were incubated with 40 nM Novo-TRX and incubated for 1 hour before the binding was measured. The average FP signal (mP) for four replicates was determined and the error bars represent the standard deviation. To determine the $K_D$, the data were fit using a sigmoidal dose-response equation.

FIG. 4: The effect of common additives on the binding of Novo-TRX to GyrB. Common buffer additives were tested for their ability to alter the interaction of 40 nM Novo-TRX with 40 nM GyrB in a homogeneous FP binding assay. The average FP signal (mP) for four replicates was determined and the error bars represent the standard deviation. A) DMSO and the non-ionic detergents, TritonX-100 and Tween-20, were tested from 0-50% (v/v) and 0-10% (v/v), respectively. B) BSA was tested from 0-1000 mg/mL (0 to 15 μM).

Figures 5A, 5B:
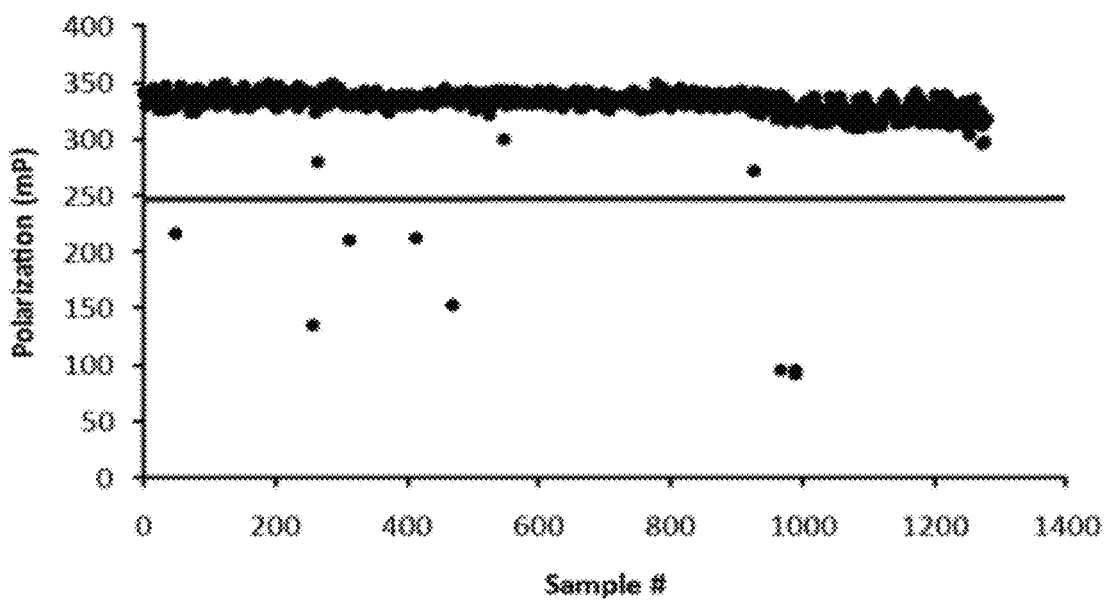
Figure 5C:
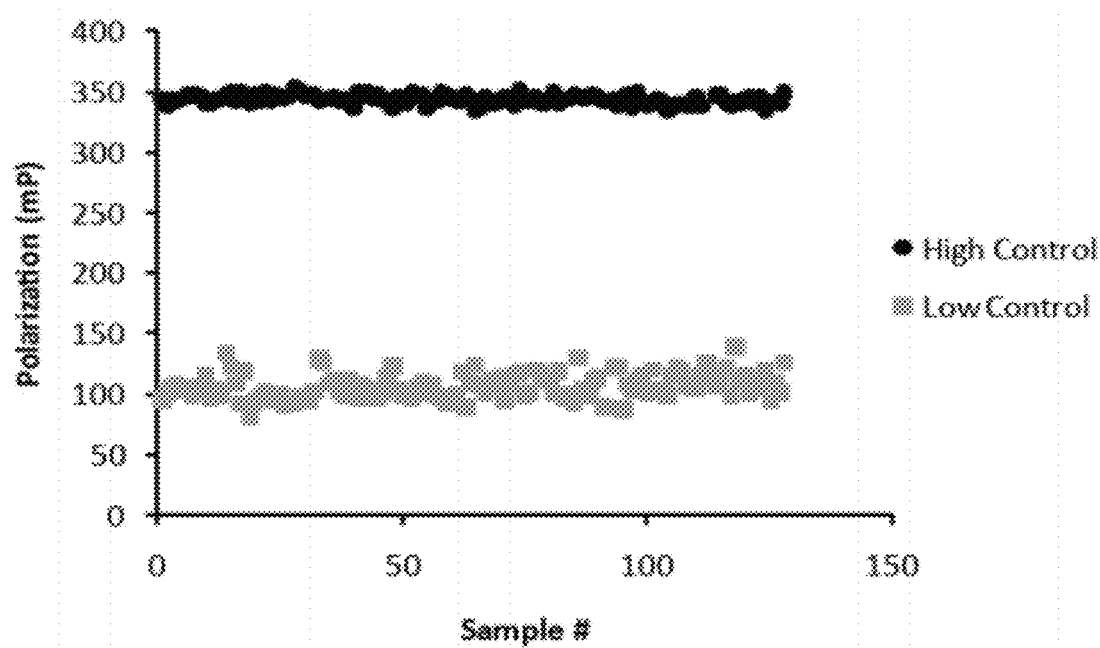
Figure 5D:
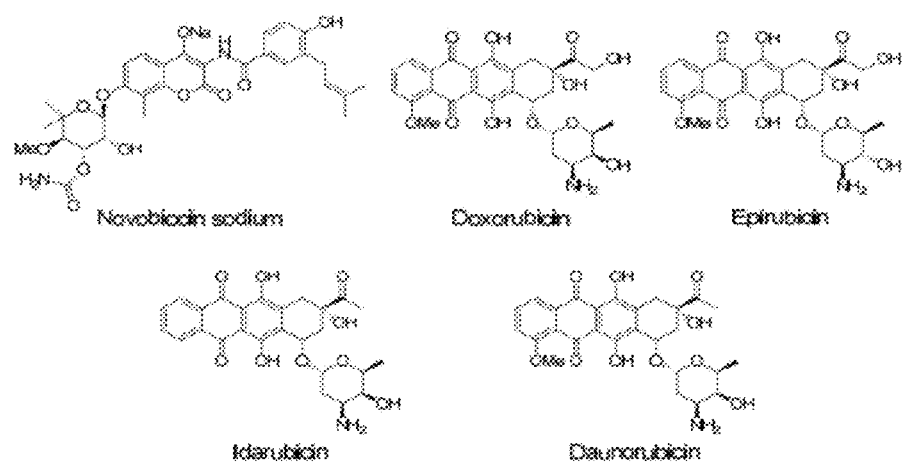

FIG. 5: HTS of FDA-approved drugs for inhibitors of Novo-TRX binding to GyrB. A small HTS of a library of FDA-approved compounds and 80 additional antibiotics (in triplicate) was performed in 384-well microplate format to validate the usefulness of the FP assay in identifying inhibitors of Novo-TRX binding to GyrB. A) A summary and statistical analysis of the HTS with the Z'-factor, Z-factor, signal-to-noise (S/N) and signal-to-background (S/B) ratios were calculated according to Zhang et al[15]. B) Compounds were screened at a final concentration of 10 μM for the ability to inhibit the interaction of 40 nM Novo-TRX with 40 nM GyrB. Shown is the FP signal (mP) for each sample. A hit was classified as a compound that inhibited greater than 40% of the binding of Novo-TRX to GyrB. C) Each plate also contained 32 high signal control samples (DMSO) and 32 low signal control samples (10 μM Novobiocin). D) Two classes of compounds were identified from the 7 compounds found to inhibit the binding of Novo-TRX to GyrB by at least 40%. Novobiocin, a known inhibitor of GyrB and our positive control, was identified in 4 separate locations. The remaining hits are members of the anthracycline family of cancer chemotherapeutics which are known to have anti-topoisomerase (gyrase) activity.

Figure 6:
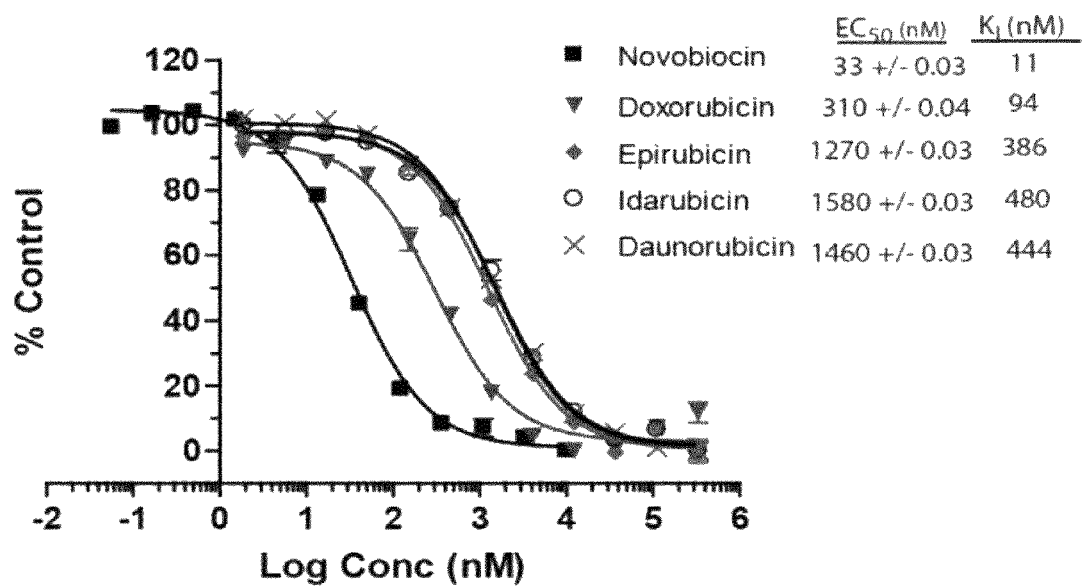

FIG. 6: The $K_I$ of hits from the HTS. Dose-response experiments for the hits from the screen were performed using the FP assay to monitor the inhibition of the binding of 40 nM Novo-TRX to 40 nM GyrB. The average FP signal for each quadruplicate was calculated and normalized to the DMSO control sample. The error bars represent standard deviation of four replicates. The $EC_{50}$ and $K_I$ values were determined using the sigmoidal dose-response equation in GraphPad Prism 4.

Figure 7:
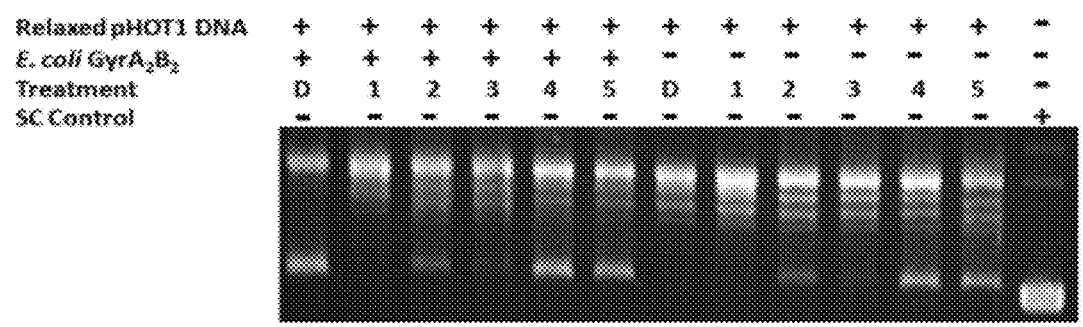

FIG. 7: A secondary Gyr activity assay to confirm hits from the HTS. A secondary assay using the *E. coli* Gyr $A_2B_2$ heterotetramer was used to confirm that the hits from the HTS were able to prevent the supercoiling of 0.5 μg of the relaxed plasmid DNA (pHOT1). Reactions with and without the gyrase heterotetramer were incubated for 1 hour with 50 μM of Novobiocin (1), Doxorubicin (2), Epirubicin (3), Idarubicin (4), Daunorubicin (5), or DMSO (D) and the conversion of relaxed plasmid DNA to supercoiled (SC) DNA was analyzed by electrophoresis on an agarose gel and detected with ethidium bromide staining. Relaxed DNA and SC DNA were included as positive and negative controls, respectively.

Reagents

All chemicals were purchased from Sigma-Aldrich Chemical Company (St. Louis, Mo.) unless otherwise noted.

Synthesis of Novo-TRX

The Novo-TRX probe was synthesized by attaching a reactive secondary amine to novobiocin through a Mannich reaction followed by conjugation to the Texas Red-X fluorescent dye. To produce the reactive novobiocin amine intermediate, novobiocin sodium (400 mg, 0.62 mmol), paraformaldehyde (10.5 mg, 0.69 mmol), methyl-amine (471 μL, 0.94 mmol from 2M THF solution), and acetic acid (56 μL, 0.94 mmol) were sealed in a glass microwave reactor vial with 4 mL of anhydrous THF. After the mixture was heated for 3 hours at 115° C., the solvent was removed under reduced pressure. The crude reaction was purified by preparative HPLC to yield 115 mg of the pure product, which was confirmed by LC/MS and $^1$H-NMR analysis. The novobiocin amine intermediate (3.7 mg, 4.6 μmol) was dissolved in dry DMF (200 μL) before Texas Red-X SE (Invitrogen, 2.5 mg, 3.0 μmol) and triethylamine (50 μL) were added. The reaction was shaken for 2 hours at room temperature and then the entire mixture was directly injected onto the preparative HPLC system running with acetonitrile and water (0.1% TFA) to yield the pure Novo-TRX probe. The structure of Novo-TRX was confirmed by LC/MS and $^1$H-NMR analysis.

Overexpression Plasmids

GyrB was cloned into a pET28 expression plasmid (Novagen, Madison, Wis.) by polymerase chain reaction (PCR) from genomic DNA isolated from *F. tularensis* Schu S4. Primers were selected to add an amino-terminal His$_6$-tag. The reverse primer also added NheI and XhoI restriction enzyme sites, respectively. The sequence of GyrB was confirmed to be identical to the published source[14].

Protein Expression and Purification

*F. tularensis* GyrB was produced from *E. coli* BL21 Star (DE3) (Invitrogen, Carlsbad, Calif.) that carried the GyrB pET28 expression vector as described above. Briefly, GyrB was grown in Luria-Bertani (LB) media at 37° C. until an optical density (OD)$_{600}$ of 0.4 was reached and then induced with 1 mM isopropyl β-D-1-thiogalactopyranoside (IPTG). Bacteria were grown for 3 hours at 30° C. after induction and then collected through centrifugation. The cell pellet was resuspended in TGE (50 mM Tris-HCl pH 7.9, 5% glycerol, and 0.5 mM ethylenediaminetetraacetic acid [EDTA]) and incubated with 250 μg/mL lysozyme for 20 minutes at 4° C. Bacteria were lysed using sonication (4×30 seconds, 70% amplitude) and then centrifuged for 25 minutes at 22,000×g to remove cell debris.

GyrB was isolated from the supernatant fraction of the *E. coli* lysate by a multistep purification procedure using the AKTA Explorer (GE Healthcare, Piscataway, N.J.). To begin, the supernatant was loaded onto a 5-mL HiTrap Heparin column (GE Healthcare) equilibrated with TGE. Unbound material was washed from the column and protein was eluted with a 0-1M NaCl gradient over 10 column volumes (CV) with a flow rate of 4 mL/minute, and 4 mL fractions were collected. Fractions containing GyrB were pooled, and guanidine HCl was added to produce a final concentration of 0.3 M. The pooled fractions were then loaded onto a 5-mL HisTrap nickel column (GE Healthcare) that was equilibrated with the low imidazole buffer (500 mM NaCl, 50 mM Tris-HCl pH 7.9, 20 mM imidazole, and 0.01% Tween-20). The protein was eluted using a buffer containing 400 mM imidazole over 15 CV with a flow rate of 3 mL/minute, and 3 mL fractions were collected. The pooled fractions containing GyrB were then loaded onto a 120-mL Sephacryl 16/60 S-200 HR size exclusion column (GE Healthcare) pre-equilibrated with a buffer containing 200 mM NaCl, 50 mM Tris-HCl pH7.9, 0.5 mM EDTA, 5% glycerol, 1 mM dithiothreitol (DTT), and 5 mM $MgCl_2$. An isocratic elution was performed with a flow rate of 1 mL/minute for 1.5 CV, and 5 mL fractions were collected. Fractions containing purified GyrB were pooled and dialyzed into storage buffer (25 mM NaCl, 50 mM Tris-HCl pH7.9, 0.5 mM EDTA, 50% glycerol, 1 mM DTT, and 5 mM $MgCl_2$) using a 12 mL Slide-A-Lyzer, 10,000 MWCO (Thermo Scientific, Rockford, Ill.).

Equilibrium Binding Experiment

Association binding experiments were performed to determine the time necessary for the binding of Novo-TRX and GyrB to reach equilibrium. These experiments were performed in quadruplicate in a volume of 20 μL of the assay buffer (25 mM NaCl, 50 mM Tris-HCl pH 7.9, 0.5 mM EDTA, 5 mM $MgCl_2$, 5 mM DTT, 5% glycerol) in black, flat-bottom polystyrene NBS 384-well microplates (Corning, Corning, N.Y.). To initiate the experiment, an equal volume of 2× Novo-TRX was added to 2× GyrB to produce a final concentration of 40 nM GyrB and 10, 50, or 100 nM Novo-TRX. The level of FP was determined using an Analyst HT plate reader (Molecular Devices, Sunnyvale, Calif.) by exciting at 560 nm with polarized light through a Q595 long-pass dichroic minor and measuring the amount of parallel and perpendicular light at 645 nm with medium attenuation. The binding of Novo-TRX to GyrB was measured every 30 seconds for 70 cycles. Upon completion of the association experiments, a 125-fold excess of unlabeled novobiocin (10 µM final concentration) was added and the change in polarization was monitored every 30 seconds for 70 cycles to measure the dissociation. The dissociation data were fit using a one-phase exponential decay equation, Y=Span*exp(−K*X)+Plateau by GraphPad Prism 4 (GraphPad Software, San Diego, Calif.) to determine the average half-life of dissociation.

Saturation Binding Experiment

Binding experiments were performed in quadruplicate to determine the strength of the interaction ($K_D$) of Novo-TRX with GyrB using a method that closely mimics the desired order of addition used in the high control samples of the HTS. A serial dilution of 3× GyrB (0-2500 nM final concentration) was made in the assay buffer and mixed with an equal volume (7 µL) of 3X Novo-TRX (40 nM final concentration). The mixture was then diluted with the assay buffer+15% dimethyl sulfoxide (DMSO) to result in the final concentrations of Novo-TRX, GyrB, and 5% DMSO. The samples were incubated for 1 hour and the FP was measure as described above. To determine the $K_D$, the data were fit using the sigmoidal dose-response equation, Y=Bottom+(Top-Bottom)/(1+10^($LogEC_{50}$-X)), in GraphPad Prism 4.

Solvent Susceptibility Experiment

Standard additives for drug screening were tested for their effect on the binding of 40 nM Novo-TRX to 40 nM GyrB. The following components were tested: DMSO, TritonX-100, Tween-20, and bovine serum albumin (BSA). Quadruplicate serial dilutions of a 2× stock of each component were made (10 µL final volume) in black, flat-bottom polystyrene NBS 384-well microplates (Corning). To measure the FP, 15 µL of a 2× complex (80 nM Novo-TRX, 80 nM GyrB) in 2× assay buffer (50 mM NaCl, 100 mM Tris-HCl pH 7.9, 1.0 mM EDTA, 10 mM $MgCl_2$, 10 mM DTT, 10% glycerol) were added to 15 µL of a 2× serial dilution of the various components (20 µL total volume, final concentration of 40 nM Novo-TRX/40 nM GyrB in assay buffer) and incubated covered for 1 hour at 25° C. (room temperature). After the incubation, the FP signal was measured as described above.

High-Throughput Screening of a Small Chemical Library

A small chemical library comprising 1040 FDA-approved drugs (one replicate of each) and 80 additional antibiotics (three replicates of each) were used to validate the use of the GyrB FP assay in identifying inhibitors of the ATP-binding pocket through HTS. Compounds were screened in a 384-well format at a final concentration of 10 µM. Each plate was composed of 320 test compounds, 32 negative controls (5% DMSO), and 32 positive controls (10 µM novobiocin). To perform the screen, 14 µL of a 1.5× master mix of 60 nM Novo-TRX/60 nM GyrB was added to all the wells using the WellMate bulk liquid dispenser (Thermo Scientific). The PlateMate Plus liquid handler (Thermo Scientific) was then used to add 7 µL of the positive and negative controls to the plate, and then 7 µL of the test compounds in 15% DMSO were added to the plates, resulting in a final concentration of 40 nM Novo-TRX, 40 nM GyrB, 10 µM compound, and 5% DMSO. The plates were incubated for 1 hour at room temperature, and the FP signal was measured as described above. The Z'-factor, Z-factor, and signal-to-noise (S/N) and signal-to-background (S/B) ratios were calculated as described by Zhang et al[15].

Dose-Response Experiment

The ability of the hits identified in the HTS to disrupt the interaction of Novo-TRX with GyrB was confirmed using an FP dose-response experiment. In brief, 40 nM Novo-TRX was used along with 40 nM GyrB in black 384-well plates. Quadruplicate stocks of the compounds were made by first diluting the compound (stored in 100% DMSO) 10-fold into the assay buffer+15% DMSO then serially diluting 3-fold with assay buffer+15% DMSO to yield 3× compound concentration; 7 µL of the compounds were then mixed with 14 µL of a 1.5× mixture of Novo-TRX/GyrB to give a final volume of 21 µl and 5% DMSO. The FP was read after 1 hour incubation at room temperature as described above. The background signal was subtracted and the FP signal was normalized to the DMSO control. Data were plotted and fitted, and the $K_1$ values were calculated using the sigmoidal dose-response equation in the GraphPad Prism 4 software.

Gyrase Activity Assay

Gyrase activity was measured using the purified *Escherichia coli* DNA Gyrase and Relaxed DNA kit (Topogen, Port Orange, Fla.) according to the manufacturer's instructions. Briefly, the *E. coli* gyrase holoenzyme was incubated with 0.5 µg of the relaxed pHOT1 DNA for 1 hour at 37° C. and the level of supercoiling was measured by agarose-gel electrophoresis. DNA was visualized with ethidium bromide staining.

REFERENCES

1. Marko O, Miha K, Tom S: Discovery and Development of ATPase Inhibitors of DNA Gyrase as Antibacterial Agents. *Current Medicinal Chemistry* 2007; 14:2033-2047.
2. Nakada N, Gmünder H, Hirata T, Arisawa M: Characterization of the Binding Site for Cyclothialidine on the B Subunit of DNA Gyrase. *J Biol Chem* 1995; 270:14286-14291.
3. Hooper D C, Wolfson J S, Ng E Y, Swartz M N: Mechanisms of action of and resistance to ciprofloxacin. *Am J Med* 1987; 82:12-20.
4. Smith J T: The mode of action of 4-quinolones and possible mechanisms of resistance. *J Antimicrob Chemother* 1986; 18 Suppl D:21-29.
5. Gross C H, Parsons J D, Grossman T H, Charifson P S, Bellon S, Jernee J, Dwyer M, Chambers S P, Markland W, Botfield M, Raybuck S A: Active-Site Residues of *Escherichia coli* DNA Gyrase Required in Coupling ATP Hydrolysis to DNA Supercoiling and Amino Acid Substitutions Leading to Novobiocin Resistance. *Antimicrob Agents Chemother* 2003; 47:1037-1046.
6. Boehm H J, Boehringer M, Bur D, Gmuender H, Huber W, Klaus W, Kostrewa D, Kuehne H, Luebbers T, Meunier-Keller N, Mueller F: Novel Inhibitors of DNA Gyrase: 3D Structure Based Biased Needle Screening, Hit Validation by Biophysical Methods, and 3D Guided Optimization. A Promising Alternative to Random Screening. *J Med Chem* 2000; 43:2664-2674.
7. Reece R J, Maxwell A: Tryptic fragments of the *Escherichia coli* DNA gyrase A protein. *J Biol Chem* 1989; 264: 19648-19653.
8. Roychoudhury S, Makin K M, Twinem T L, Stanton D T, Nelson S L, Catrenich C E: Development and use of a high-throughput bacterial DNA gyrase assay to identify mammalian topoisomerase II inhibitors with whole-cell anticancer activity. *J Biomol Screen* 2003; 8:157-163.
9. Burrell M R, Burton N P, Maxwell A: A high-throughput assay for DNA topoisomerases and other enzymes, based on DNA triplex formation. *Methods Mol Biol* 2010; 613: 257-266.
10. Moir D T, Ming D, Opperman T, Schweizer H P, Bowlin T L: A high-throughput, homogeneous, bioluminescent assay for *Pseudomonas aeruginosa* gyrase inhibitors and other DNA-damaging agents. *J Biomol Screen* 2007; 12:855-864.
11. Owicki J C: Fluorescence polarization and anisotropy in high throughput screening: perspectives and primer. *J Biomol Screen* 2000; 5:297-306.
12. Roehrl M H, Wang J Y, Wagner G: A general framework for development and data analysis of competitive high-throughput screens for small-molecule inhibitors of protein-protein interactions by fluorescence polarization. *Biochemistry* 2004; 43:16056-16066.
13. Lamour V, Hoermann L, Jeltsch J M, Oudet P, Moras D: An open conformation of the *Thermus thermophilus* gyrase B ATP-binding domain. *J Biol Chem* 2002; 277: 18947-18953.
14. Larsson P, Oyston P C, Chain P, Chu M C, Duffield M, Fuxelius H H, Garcia E, Halltorp G, Johansson D, Isherwood K E, Karp P D, Larsson E, Liu Y, Michell S, Prior J, Prior R, Malfatti S, Sjostedt A, Svensson K, Thompson N, Vergez L, Wagg J K, Wren B W, Lindler L E, Andersson S G, Forsman M, Titball R W: The complete genome sequence of *Francisella tularensis*, the causative agent of tularemia. *Nat Genet* 2005; 37:153-159.
15. Zhang J H, Chung T D, Oldenburg K R: A Simple Statistical Parameter for Use in Evaluation and Validation of High Throughput Screening Assays. *J Biomol Screen* 1999; 4:67-73.
16. Holdgate G A, Tunnicliffe A, Ward W H, Weston S A, Rosenbrock G, Barth P T, Taylor I W, Pauptit R A, Timms D: The entropic penalty of ordered water accounts for weaker binding of the antibiotic novobiocin to a resistant mutant of DNA gyrase: a thermodynamic and crystallographic study. *Biochemistry* 1997; 36:9663-9673.
17. Gabbay E J, Grier D, Fingerle R E, Reimer R, Levy R, Pearce S W, Wilson W D: Interaction specificity of the anthracyclines with deoxyribonucleic acid. *Biochemistry* 1976; 15:2062-2070.
18. Khan F, Sherwani A F, Afzal M: Chromosomal aberration and micronucleus studies of two topoisomerase (II) targeting anthracyclines. *J Environ Biol* 2009; 30:409-412.
19. Saffi J, Agnoletto M H, Guecheva T N, Batista L F, Carvalho H, Henriques J A, Stary A, Menck C F, Sarasin A: Effect of the anti-neoplastic drug doxorubicin on XPD-mutated DNA repair-deficient human cells. *DNA Repair (Amst)* 2010; 9:40-47.
20. Bodley A, Liu L F, Israel M, Seshadri R, Koseki Y, Giuliani F C, Kirschenbaum S, Silber R, Potmesil M: DNA topoisomerase II-mediated interaction of doxorubicin and daunorubicin congeners with DNA. *Cancer Res* 1989; 49:5969-5978.
21. Viglasky V, Valle F, Adamcik J, Joab I, Podhradsky D, Dietler G: Anthracycline-dependent heat-induced transition from positive to negative supercoiled DNA. *Electrophoresis* 2003; 24:1703-1711.
22. Waring M: Variation of the supercoils in closed circular DNA by binding of antibiotics and drugs: evidence for molecular models involving intercalation. *J Mol Biol* 1970; 54:247-279.

The descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A fluorescence polarization probe comprising an aminocoumarin conjugated to a fluorescent label, said probe operative as a fluorescent polarization probe of the ATP-binding site of prokaryotic DNA gyrase B or topoisomerase IV E subunit, wherein the aminocoumarin is a 3-amino-4,7-dihydroxycumarin ring moiety linked with a sugar moiety in 7-position and a benzoic acid derivative moiety in 3-position, and the fluorescent probe is linked to the benzoic acid derivative moiety;

the aminocoumarin is novobiocin or clorobiocin;
the fluorescent label is an acridine, a cyanine, a fluorone, an oxazin, a phenanthridine, a rhodamine or a BODIPY (boron-dipyrromethene); and
the subunit is gyrase, B subunit of *Francisella tularensis*.

2. The probe of claim 1 comprising structure I:

3. The probe of claim 1 wherein the aminocoumarin is novobiocin.
4. The probe of claim 1 wherein the fluorescent label is a rhodamine.
5. The probe of claim 1 wherein the fluorescent label is Texas Red-X.

6. The probe of claim 1 wherein the aminocoumarin is a 3-amino-4,7-dihydroxycumarin ring moiety linked with a sugar moiety in 7-position and a benzoic acid derivative moiety in 3-position, and the fluorescent probe is linked to the benzoic acid derivative moiety;
the aminocoumarin antibiotic is novobiocin;
the fluorescent label is Texas Red-X; and
the subunit is gyrase, B subunit is of *Francisella tularensis*.

7. A method of making the probe of claim 1, comprising the step of:
conjugating the label through a reactive secondary amine of an aminocoumarin amine to form the probe.

8. A method of making the probe of claim 1, comprising the steps of:
attaching a reactive secondary amine to the aminocoumarin through a Mannich reaction to form an aminocoumarin amine; and
conjugating the label through the reactive secondary amine of the aminocoumarin amine to form the probe.

9. A method of detecting binding of the probe of claim 1 to the subunit, comprising the step of: detecting fluorescence polarization of the probe in a mixture of the probe and the subunit.

10. A method of detecting binding of the probe of claim 2 to the subunit, comprising the step of: detecting fluorescence polarization of the probe in a mixture of the probe and the subunit.

11. A method of detecting binding of the probe of claim 5 to the subunit, comprising the step of: detecting fluorescence polarization of the probe in a mixture of the probe and the subunit.

12. A method of detecting binding of the probe of claim 6 to the subunit, comprising the step of: detecting fluorescence polarization of the probe in a mixture of the probe and the subunit.

13. The method of claim 9 wherein the mixture further comprises a topoisomerase inhibitor that inhibits binding of the probe to the subunit.

14. The method of claim 10 wherein the mixture further comprises a topoisomerase inhibitor that inhibits binding of the probe to the subunit.

15. The method of claim 11 wherein the mixture further comprises a topoisomerase inhibitor that inhibits binding of the probe to the subunit.

16. The method of claim 12 wherein the mixture further comprises a topoisomerase inhibitor that inhibits binding of the probe to the subunit.

17. The method of claim 9 wherein the mixture further comprises a topoisomerase inhibitor that inhibits binding of the probe to the subunit, wherein the method is in a high-throughput format and repeated in parallel with a plurality of candidate topoisomerase inhibitors.

18. The method of claim 10 wherein the mixture further comprises a topoisomerase inhibitor that inhibits binding of the probe to the subunit, wherein the method is in a high-throughput format and repeated in parallel with a plurality of candidate topoisomerase inhibitors.

19. The method of claim 11 wherein the mixture further comprises a topoisomerase inhibitor that inhibits binding of the probe to the subunit, wherein the method is in a high-throughput format and repeated in parallel with a plurality of candidate topoisomerase inhibitors.

20. The method of claim 12 wherein the mixture further comprises a topoisomerase inhibitor that inhibits binding of the probe to the subunit, wherein the method is in a high-throughput format and repeated in parallel with a plurality of candidate topoisomerase inhibitors.

* * * * *

UNITED STATES PATENT AND TRADEMARK OFFICE
CERTIFICATE OF CORRECTION

Page 1 of 1

PATENT NO. : 8,497,361 B2
APPLICATION NO. : 13/215175
DATED : July 30, 2013
INVENTOR(S) : Peter Madrid et al.

It is certified that error appears in the above-identified patent and that said Letters Patent is hereby corrected as shown below:

In The Specification

The government support paragraph at col. 1, lines 6-8 should read as follows:

This invention was made with government support under Grant Number 1U01AI082070-01 awarded by National Institutes of Health (NIH); The government has certain rights in the invention.

Signed and Sealed this
Nineteenth Day of April, 2016

Michelle K. Lee
*Director of the United States Patent and Trademark Office*